United States Patent [19]
Koenig, Jr.

[11] Patent Number: 4,785,868
[45] Date of Patent: Nov. 22, 1988

[54] MEDICAL NEEDLE AND METHOD FOR MAKING

[75] Inventor: Marvin E. Koenig, Jr., Roseville, Minn.

[73] Assignee: Titan Medical, Inc., Arden Hills, Minn.

[21] Appl. No.: 58,178

[22] Filed: Jun. 4, 1987

[51] Int. Cl.⁴ .............................................. B21G 3/28
[52] U.S. Cl. ......................................... 163/5; 72/379; 206/370; 206/380; 604/161; 604/272
[58] Field of Search ................................ 163/1, 4, 5, 6; 206/382, 380, 383, 370; 604/160, 161, 272; 72/404, 332, 379

[56] References Cited

U.S. PATENT DOCUMENTS 3,359,978 12/1967 Smith, Jr. .
4,100,393 7/1978 Luther .
4,377,165 3/1983 Luther et al. .
4,449,973 4/1984 Luther .
4,605,279 8/1986 Mixon .............................. 72/404 X
4,672,734 6/1987 Kawada et al. .................... 163/1 X Primary Examiner—Mark Rosenbaum
Attorney, Agent, or Firm—Merchant, Gould, Smith, Edell, Welter & Schmidt

[57] ABSTRACT

A progressive die process for making medical needles attached to a carrier strip, as well as the product of the process. The process includes steps of forming a flat blank in unitary attachment with a carrier strip and coining edges of the tip of each flat blank, arcuately shaping the blank, and closeably forming the arcuate blank to create a medical needle having a holding portion, a cannulated portion and a tip. In addition, the cannulated portion may be encased for fluid delivery or grooved so the needle may be split.

4 Claims, 4 Drawing Sheets

MEDICAL NEEDLE AND METHOD FOR MAKING

TECHNICAL FIELD

The present invention is directed to the field of medical devices, and more particularly, to medical needles. The term medical needles is understood to include, for example, needles used to direct the flow medicines or other fluids, and needles used as cannulas.

BACKGROUND OF THE INVENTION

Medical devices are made with great care. Medical needles have traditionally been made on an individual basis and have, consequently, been relatively expensive to produce. Several patents disclose exemplary manufacturing processes.

U.S. Pat. No. 3,359,978 to R. M. Smith, Jr., discloses a process beginning with stamping a needle pattern from steel flat stock. A groove or trough is formed in the flat stock to provide a weakened region for needle separation when used for catheter implacement. The flat stock is then rolled to a circular needle configuration. Alternatively, Smith describes a process whereby flat sheet stock is first formed into a tube, and then grooves on opposite sides of the tube are milled along the exterior. Thereafter, wings or flaps are soldered, welded or braised to the tube for needle splitting purposes. In either case, the needle tip is sharpened after the tubular shape is formed.

U.S. Pat. No. 4,100,393 to Ronald B. Luther describes a process beginning with tube stock which is cut, beveled at one end, and flared at the other end. A laser is used to weld wings at the appropriate location to the tubular needle. The laser is also used to provide a score line on one side from one end of the needle to the other and a cut line on the other side. To complete the tip, the beveled surfaces are honed.

U.S. Pat. No. 4,377,165 to Ronald B. Luther shows a somewhat different process. This process comprises continuously forming a needle blank from flat sheet metal or from a roll. A groove of controlled depth is formed along the blank stock which thereafter is rolled to a hollow configuration and then cut into individual needle barrels with a longitudinal slit parallel to and on the opposite side of the barrel as the groove. The needle ends are formed and wings are welded on opposite sides of the groove.

U.S. Pat. No. 4,449,973 to Ronald B. Luther shows still another process for making a medical needle. In this patent, Luther forms a groove on flat stock and then rolls the flat stock into a barrel. The groove may even be partial slits. Thereafter, the barrel may be hardened by cold drawing it into a smaller diameter and laser welding it partially closed at any slit apparently to improve cannula strength. The needle tip is ground and the end opposite is formed for mounting into wing holders.

Thus, the known art discloses a number of different techniques for making medical needles. Each of the techniques, however, is directed to working with a single needle at a time. As a resut, the manufacturing process, regardless of type, is relatively expensive. The present invention is directed to a process and the produce of the process wherein a plurality of medical needles are formed through a series of steps which leave individual needles unitarily attached to a part of the steel stock as a carrier strip.

SUMMARY OF THE INVENTION

The present invention is directed to a method for manufacturing medical needles and the produce manufactured thereby. The medical needle product includes a transverse strip and a plurality of medical needles unitarily attached to the strip. Each of the medical needles includes a tip, a hub, and a cannulated portion extending between the tip and the hub.

The needle utilizes a roll of sheet metal which is formed into the medical needles and carries strip. The process includes a step of forming a flat blank in unitary attachment with a carrier strip. Tip edges are coined. A following step includes forming with a set of first dies the blank into an arcuate shape. A further step includes closeably forming with a set of second dies the arcuately shaped blank to form the hub, the cannulated portion and the tip. During this step, the blank is shaped so that the opposite edges of the cannulated portions are moved into facing proximity with one another.

The present progressive die process is particularly advantageous since for the first time medical needles may be produced at a high quality with many possible custom features, and at a lower cost than present needles manufactured one at a time. In addition, as a result of providing medical needles attached on a continuous strip, subsequent users experience less cost with respect to handling, inspection, further processing, and assembly with related devices.

The process includes a step wherein edges of the tip of each medical needle are coined. Such operation allows for a precise forming of sharp edges in virtual elimination of any burrs. In this regard, the opening at the tip of the passageway through the cannulated portion can include both sharpened edges and dull edges. In addition, the tip can be formed in various well-known shapes, including Toughy, Huber, bevel, etc.

The medical needles of the present invention may also be made splittable by including one or more longitudinal score grooves along the cannulated portion. The scoring may be accomplished just prior to closing the cannulated portion to avoid any undue weakening of the cannulated portion. Furthermore, scoring uniformity may be quite precise since the dies can be made and controlled precisely.

A further advantage of the present invention is that not only is the metal stock handled as a roll and then unrolled during the manufacture of the medical needles, but also the metal stock need never be completely cut transversely so that the carrier strip having all the medical needles attached thereto can be rerolled at the end of the manufacturing process for subsequent ease of handling and further processing.

These many features and object of the invention are advantageous for many reasons some of which have been pointed out. The invention, however, is further explained and may be better understood by reference to the drawings and the detailed description of a preferred embodiment provided hereinafter.

DETAILED DESCRIPTION OF THE PREFERRED EMBODIMENT

Figure 1:
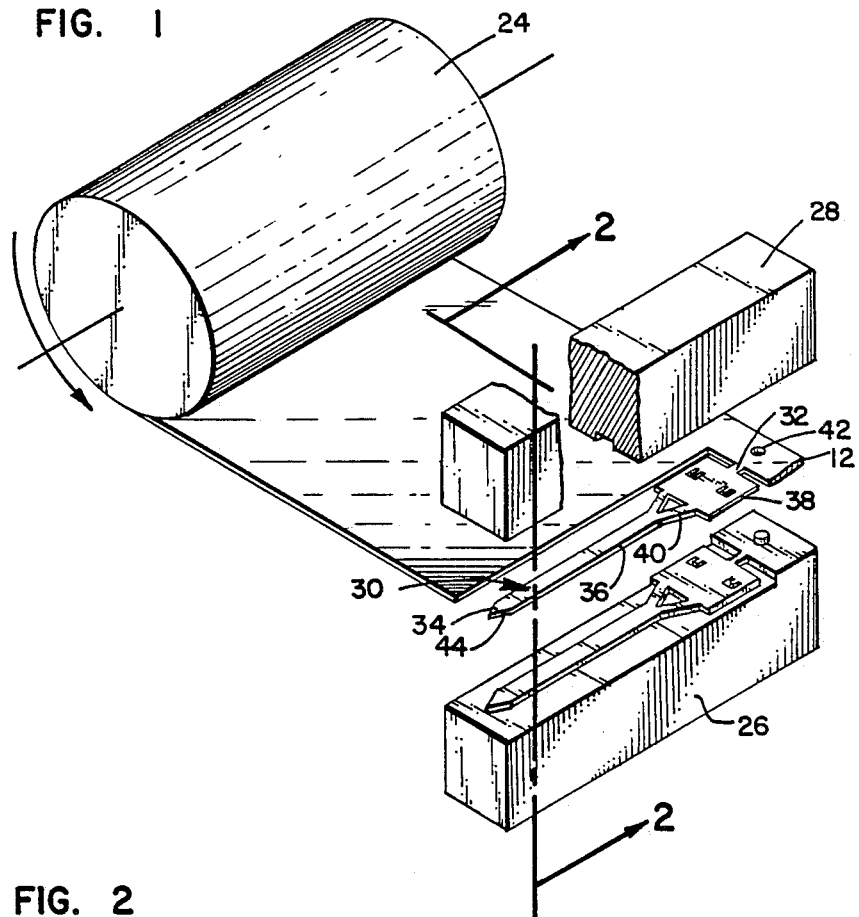
FIG. 1 is an illustration in perspective of the unrolling metal stock and die forming a flat blank step.
Figure 4:
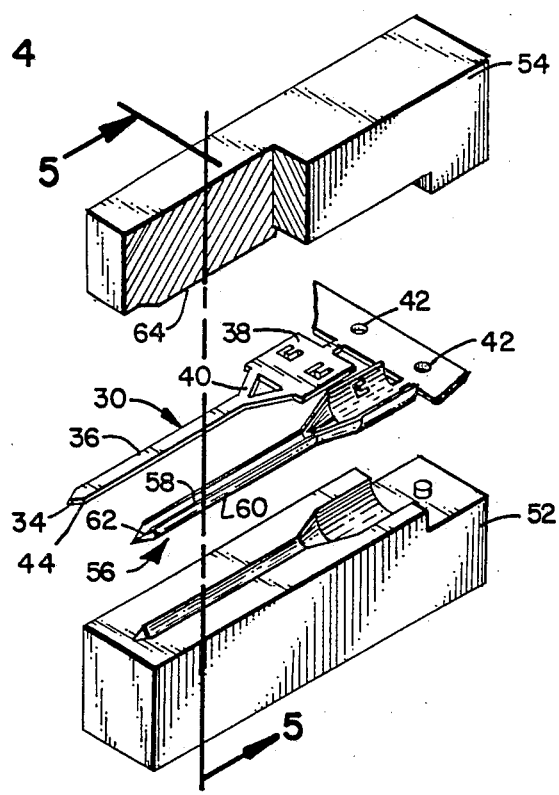
FIG. 4 is an illustration in perspective of the arcuately forming the flat blank with a set of dies step.
Figure 6:
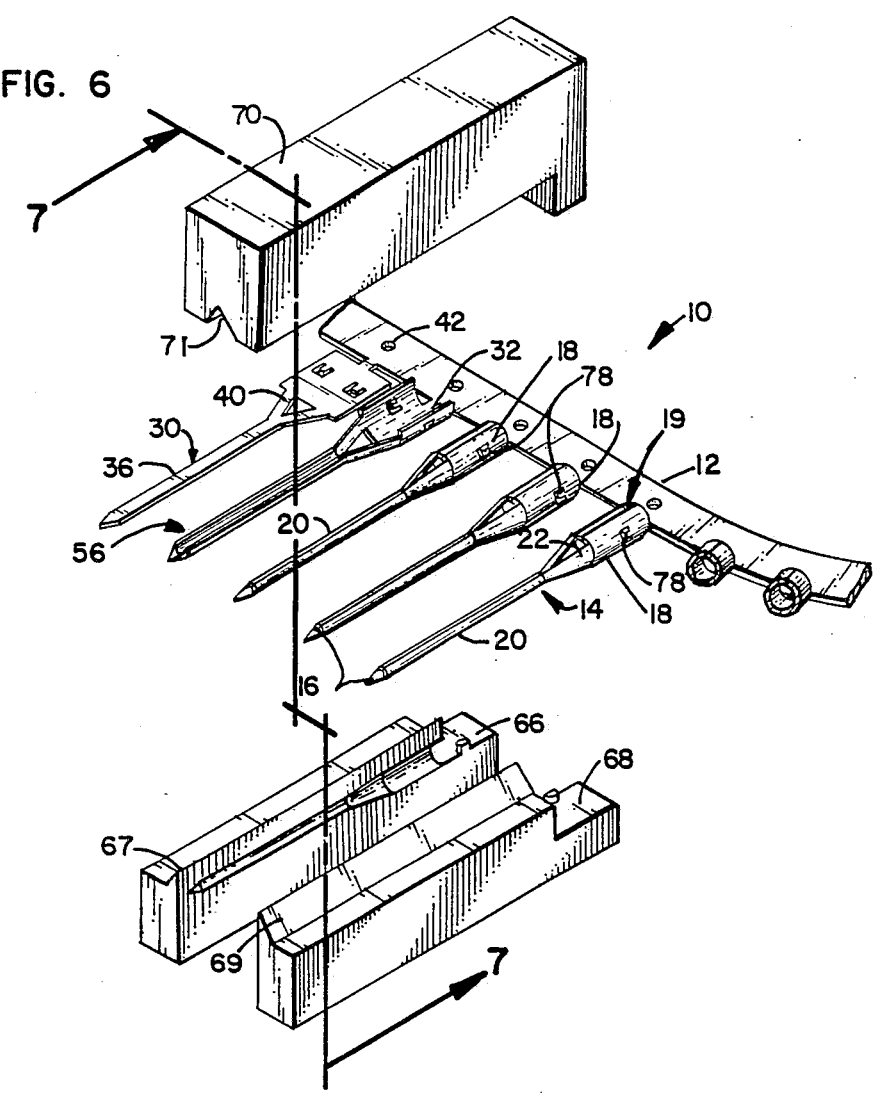
FIG. 6 is an illustration in perspective of the closeably forming step with a set of dies in accordance with the present invention.

Referring now to the drawings wherein like reference numerals designate identical or corresponding parts throughout the several views, steps of the method in accordance with the present invention are illustrated in FIGURES 1, 4 and 6. The produce apparatus of the method, designated generally as 10, is shown in FIG. 6 to include a continuous transverse strip 12 to which medical needles 14 are unitarily attached. A medical needle 14 in accordance with the present invention includes a tip 16 at the distal end, a holding portion 19 at the proximal end and a cannulated portion 20 between tip 16 holding portion 19. In addition, holding portion 19 comprises a hub 18 toward the proximal end and a connecting portion 22 between hub 18 and cannulated portion 20.

As shown in FIG. 1, the method of the present invention begins with a roll 24 of stock sheet metal, preferably a medically acceptable stainless steel grade. Roll 24 is unrolled and flattened in a known fashion before being directed into a set of dies 26 and 28 which appropriately form a flat blank 30 for needle 14. Blank 30 is in unitary attachment at neck 32 with transverse carrier strip 12. Flat blank 30 is shaped to have a portion 34 which will form tip 16, a portion 36 which will form cannulated portion 20, a portion 38 which will form hub 18 and a portion 40 which will provide the appropriate connecting portion 22 between hub 18 and cannulated portion 20. An index opening 42 is preferably formed in carrier strip 12 along the longitudinal centerline of flat blank 30.

It is noted that dies 26 and 28 are male and female dies formed appropriately to provide flat blank 30 when they are functioned in a conventional fashion. Although a set of dies 26, 28 is illustrated for use in forming flat blank 30, it is understood that some other machine, such as a wire EDM machine, could be used in the flat blank forming step to obtain equal result.

Figure 2:
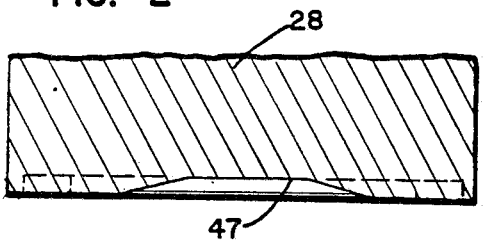
FIG. 2 is a cross-sectional view taken along line 2—2 of FIG. 1.
Figure 3:
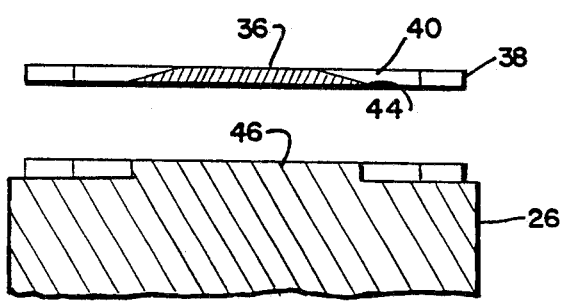
FIG. 3 is a partially cut-away perspective view of the tip of the medical needle shown in FIGS. 1 and 2.
Figure 3:
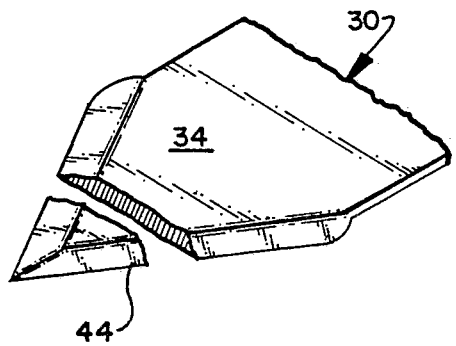

As a part of the initial step, although it is understood that more than one station of dies or an EDM machine and a set of dies, as indicated, or equivalent devices may be used, the tip 34 of flat blank 30 is coined to provide a sharp edge 44 as shown in FIGS. 2 and 3, located as desired so that edges 44 form the inside edge or the outside edge or have a location somewhere therebetween so as to provide the desired functional result. As shown in FIG. 2, the male portion 46 of die 26 is formed so that the tip is flat. The corresponding female portion 47, however, has ramped edges so that when the dies come together, the desired edge is formed, termed coined. FIG. 4 shows the desired coined result. It is clear that the edge may be located as desired by simply placing a ramp slope on each of the male and female dies or just on the male die, rather than the female die. Additionally, noncoined or square, blunt edges are formed when the dies have no ramp edges.

Figure 5:
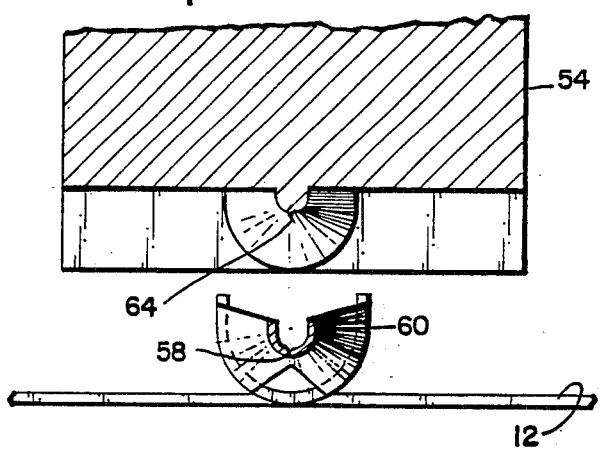
FIG. 5 is a cross-sectional view taken along line 5—5 of FIG. 4 of the dies and arcuately formed blank of FIG. 4.
Figure 5:
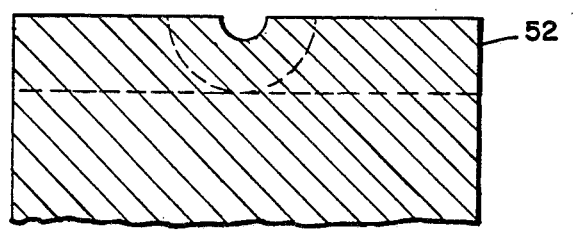

With reference to FIGS. 4 and 5, at a station subsequent to the coining of tip 34, a set of dies 52 and 54 begin to arcuately shape flat blank 30 into arcuate blank 56. The arcuate shape may be obtained with a single set of dies, such as dies 52 and 54, or there may be a plurality of stations of sets of dies which gradually increase the curvature of arcuate blank 56. During the arcuate shaping a scoring groove 58 is pressed or formed in arcuate blank 56 longitudinally along portion 60 which will become cannulated portion 20 and portion 62 which will become tip 16. Scoring line 58 is formed by an elongated protrusion 64 on male die 54.

With reference to FIG. 6, arcuate blank 56 is closeably formed to a final shape by a set of dies 66, 68 and 70 to form medical needle 14. As with the other forming steps, it is understood that, if necessary, a plurality of stations could be used to further form arcuate blank 56 into closed medical needle 14. Whereas the sets of dies illustrated in FIGS. 1 and 4 contact opposite sides of the forming part, the dies in FIG. 6 make contact only on the outside of the forming medical needle thereof. As at the station of FIG. 4, the dies of the station illustrated in FIG. 6 use the index opening 42 for alignment of the set of dies with one another and with the arcuate blank 56 which the dies are forming. Dies 66 and 68 are wedged toward one another to bend arcuately blank 56 closed as wedge halves 67 and 69 are received in groove 71 of die 70.

It has been indicated that the present process begins with a roll 24 of sheet metal. Roll 24 is unrolled before encountering the various stations discussed. When medical needles 14 have been completely formed, carrier strip 12 may be rerolled as indicated in FIG. 6 by the curvature of the formed end of transverse carrier strip 12. Preferably, a packing material would be placed between consecutive spirals.

Figure 8:
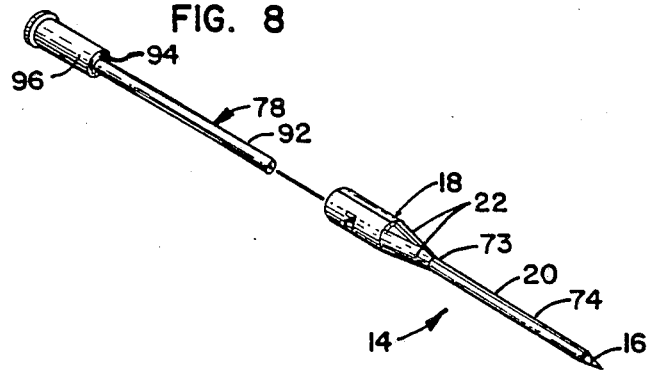
FIG. 8 is a view in perspective of a medical needle and insert for use with fluids.
Figure 7:
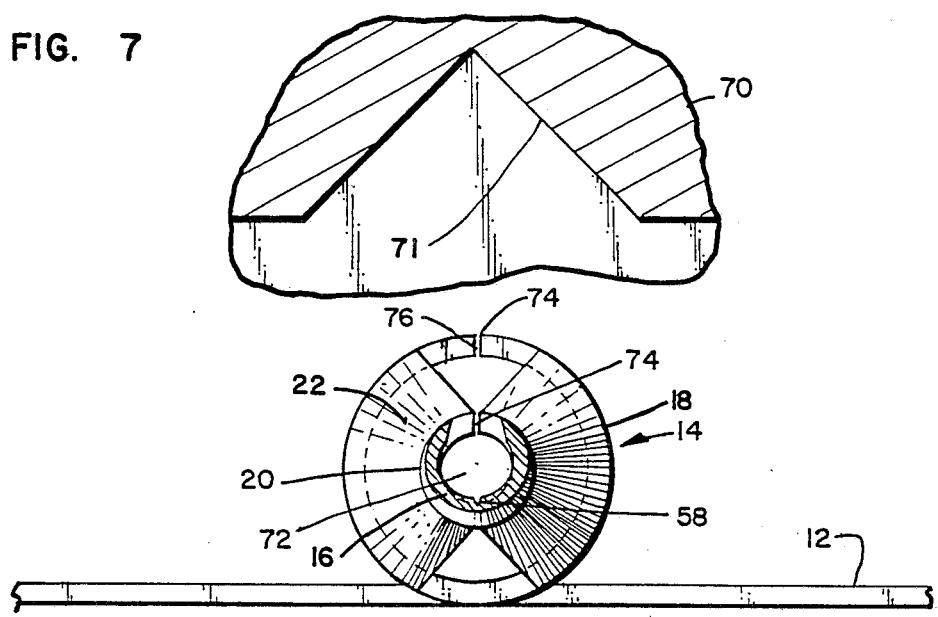
FIG. 7 is a cross-sectional view taken along line 7—7, of FIG. 6, showing a tip in cross section.
Figure 7:
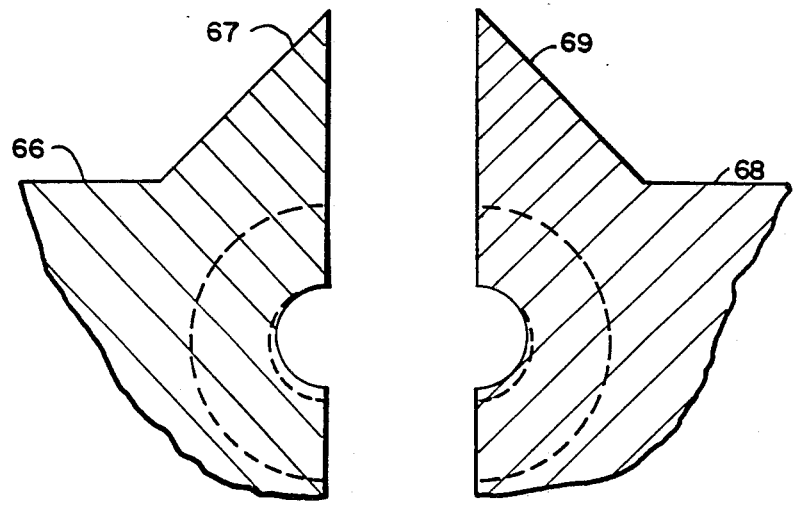

The process of making medical needles in accordance with the present invention may include a further step of encasing along cannulated portion 20 of a medical needle 14 a completely enclosed passageway 72 from the proximal end 73 of the cannulated portion 20 to tip 16 (see FIG. 8) Passageway 72 may be encased by closing groove 74 between facing longitudinal edges 76 of cannulated portion 20. Such closure could be accomplished by welding or soldering the groove 74 closed or by plating, sputtering on the inside of passageway 72, or bore coating passageway 72. In addition, as shown in FIG. 8, a separate liner 78 could be inserted into passageway 72.

Apparatus 10 is the product of the present process described herein. Apparatus 10 includes transverse carrier strip 12 and a plurality of medical needles 14. Strip 12 may be continuous for the entire length of roll 24, or strip 12 may be cut to specified lengths having a specified number of medical needles 14 attached thereto. As indicated hereinbefore, each medical needle 14 is unitarily attached to strip 12 by a connecting neck 32. Each medical needle 14 includes a tip 16, a holding portion 19 having a hub 18 and a connecting portion 22, and a cannulated portion 20 located between tip 16 and holding portion 19. Since the various dies may be formed as desired, it is possible within the principle of the present process and resultant apparatus to customize any part of medical needle 14.

Figure 9:
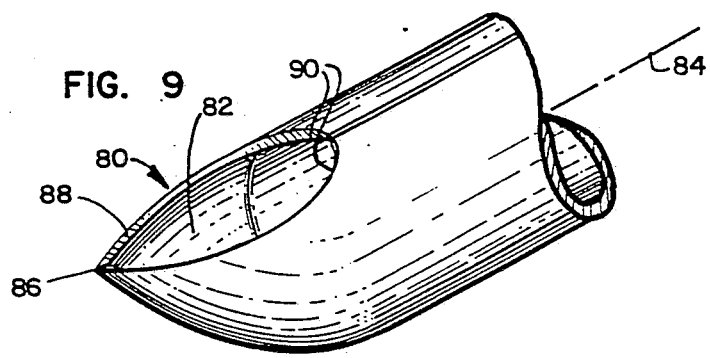
FIG. 9 is a view in perspective of an alternative tip of a type which may be formed in accordance with the present inventive process.

In this regard, tip 16 may be shaped variously from a simple ramp to shapes where the end of the tip is bent upwardly more in the shape of a boat, often termed a Toughy tip or a Huber tip depending on the particular details. As shown in FIG. 9, the Huber-like tip 80 has an opening 82 which is almost centered on a radial line extending from the axis 84 of the needle. Tip 80 proceeds from a pointed distal end 86 with sharp edges 88 gradually giving way to a dull wall 90 at the proximal end of opening 82. Proceeding from pointed end 86 in a direction opposite opening 82, the needle presents a fairly sharp V-shaped appearance which gradually widens into the cylindrical shape of the cannulated portion of the needle. The Huber-like tip is especially useful for avoiding "coring" during insertion. Regardless of the type of tip, the present progressive die process provides for coining the edges of the tip to create sharp edges exactly where desired, both longitudinally and transversely. Furthermore, as indicated, a portion of the opening edge may be dull. This contrasts with known procedures wherein the tip is ground which leads to a sharp edge all the way around the opening and whereby there is little or no control over the relative radial location of the sharp edge.

Likewise, holding portion 18 may be formed to have a variety of shapes and to include connecting portion 22 as a continuous part of hub 18. For example, the proximal end of medical needle 14 may have integral formed appendages which would appear very different from hub 18 and connecting portion 22 as shown in the figures and which would serve as a finger holder. The proximal end could be tube flared for ease of attachment to some type of other embodiment, commonly a plastic holder. The present hub 18 has a pair of tabs 78 (see FIG. 6) which are available to provide a snap-lock attachment to a holding device. Alternatively, various retention features could be formed in the hub to facilitate insert molding of an additional appendage for use with medical needle 14.

Similarly, cannulated portion 20 is formed as desired during the progressive die process. As indicated, cannulated portion 20 may be formed substantially tubular and subsequently welded or soldered or closed with some equivalent process.

As shown in FIG. 8, cannulated portion 20 may be closed by inserting a liner 78 therein. Liner 78 typically would include a tubular portion 92 which would extend from the distal end of cannulated portion 20 to a position within or beyond holding portion 18. Tubular portion 92 extends through connecting portion 22 to about the distal end of hub 18. At that location, liner 78 includes a radial wall 94 which connects a larger cylindrical portion 96 to tubular portion 94. Cylindrical portion 96 fits closely within hub 18. A distal end of cylindrical portion 96 is shaped as desired, perhaps with a Luer fitting, to mate with an additional medical tool for supplying medicinal fluid.

Alternatively, cannulated portion 20 may be made splittable by impressing a scoring groove 58 into the wall of the cannulated portion. In this regard, a scoring groove created with a die can consistently make the uniformly shaped and sized groove over the entire length of the groove due to the precision with which dies may be made and controlled. The art, on the other hand, showing a roller or a scoring bit results in a less uniform result. Furthermore, the scoring with progressive die process may be accomplished just prior to closure of the cannulated portion 20 so that there is very little premature stress on the score line.

A further significant advantage of the present process and product of the process is that the medical needles are made and are yet attached to a carrier strip. Such apparatus provides exact orientation of the medical needles 14 with all their features with respect to index openings 42 on strip 12. As a result, apparatus 10 is particularly useable for subsequent operations, such as cleaning/degreasing, polishing, any additional sharpening or grinding, spot annealing or tempering, plating or chemical etching, etc. In addition, apparatus 10 is readily packaged and shipped, easily manipulated for automatic inspection and quality control, and available for use for any automated assembly equipment.

In use, medical needle 14 is separated from carrier strip 12, possibly deburred where neck 32 connected medical needle 14 to strip 12, and inserted at hub 18 into an applicator of a type disclosed in U.S. patent applicaton Ser. No. 925,313, filed Oct. 31, 1986, hereby incorporated by reference into the present application. When used with such an applicator, medical needle 14 provides a mechanism for inserting a flexible catheter held within cannulated portion 20 through a person's skin and into a septum, vein, artery, etc. In this usage, scoring groove 58 is essential so that medical needle 14 may be retracted from the person and split for removal from the catheter.

When passageway 72 of medical needle 14 is completely encased, for example, with liner 78, then medical needle 14 may be used with a syringe or other such device for delivery of a fluid, usually a medicinal fluid.

Although such usages are indicated, it is understood that the present process may be used to make a variety of medical needle designs and, consequently, the medical needles may find a variety of uses. In addition, it is understood that the progressive die process has wide varsatility. Consequently, although the advantages and details of the process and the product created by the process are set forth at length, the disclosure thereof is exemplary. Changes made in the process or the product to the full extent extended by the general meaning of the terms on which the appended claims are expressed, are understood to be within the principle of the present invention.

What is claimed is:

1. A method for manufacturing from a roll of sheet metal medical needles unitarily attached to a carrier strip, each of said medical needles being longitudinally oriented with proximal and distal ends, each of said medical needles having a tip at the distal end, a holding portion at the proximal end, and a cannulated portion between said tip and said holding portion, said holding portion being attached to said carrier strip, said cannulated portion having opposite longitudinal edges, said method comprising the steps of:
   forming a flat blank in unitary attachment with said carrier strip and coining edges of said tip;
   forming with a set of first dies said blank into an arcuate shape; and
   closeably forming with a set of second dies said arcuately shaped blank to form said holding portion, said cannulated portion and said tip, said blank being shaped so that said opposite edges of said cannulated portion are moved into facing proximity with one another.

2. The method in accordance with claim 1 including the step of unrolling said roll of sheet metal before said first blank forming step, said method further including the step of rolling said formed sheet metal following said last closeably forming step.

3. The method in accordance with claim 1 including the step of scoring with a longitudinal groove said cannulated portion during said arcuately forming step.

4. The method in accordance with claim 1 including the step of encasing along said cannulated portion a completely enclosed passageway from said holding portion to said tip.

\* \* \* \* \*

UNITED STATES PATENT AND TRADEMARK OFFICE
CERTIFICATE OF CORRECTION

PATENT NO. : 4,785,868

DATED : November 22, 1988

INVENTOR(S) : Marvin E. Koenig, Jr.

It is certified that error appears in the above-identified patent and that said Letters Patent is hereby corrected as shown below:

Column 1, lines 64 and 65, "produce" should be--product--.

Column 2, line 4, "produce" should be--product--.

Column 2, line 10, "needle" should be--method--.

Column 2, line 11, "carries" should be--carrier--.

Column 2, line 55, "object" should be--objects--.

Column 3, line 23, "produce" should be--product--.

Column 3, line 68, "FIG. 4" should be--FIG. 3--.

Column 5, line 55, "94" should be--92--.

Signed and Sealed this

Twelfth Day of September, 1989

Attest:

DONALD J. QUIGG

Attesting Officer

Commissioner of Patents and Trademarks